(12) United States Patent
Meglan

(10) Patent No.: US 10,849,709 B2
(45) Date of Patent: Dec. 1, 2020

(54) SYSTEMS AND METHODS FOR REMOVING OCCLUDING OBJECTS IN SURGICAL IMAGES AND/OR VIDEO

(71) Applicant: Covidien LP, Mansfield, MA (US)

(72) Inventor: Dwight Meglan, Westwood, MA (US)

(73) Assignee: Covidien LP, Mansfield, MA (US)

( * ) Notice: Subject to any disclaimer, the term of this patent is extended or adjusted under 35 U.S.C. 154(b) by 117 days.

(21) Appl. No.: 16/081,193

(22) PCT Filed: Feb. 24, 2017

(86) PCT No.: PCT/US2017/019257
§ 371 (c)(1),
(2) Date: Aug. 30, 2018

(87) PCT Pub. No.: WO2017/151414
PCT Pub. Date: Sep. 8, 2017

(65) Prior Publication Data
US 2019/0053872 A1    Feb. 21, 2019

Related U.S. Application Data

(60) Provisional application No. 62/302,366, filed on Mar. 2, 2016.

(51) Int. Cl.
*G06K 9/00* (2006.01)
*A61B 90/00* (2016.01)
(Continued)

(52) U.S. Cl.
CPC ............ *A61B 90/361* (2016.02); *A61B 34/76* (2016.02); *A61B 90/00* (2016.02); *G06T 5/005* (2013.01);
(Continued)

(58) Field of Classification Search
None
See application file for complete search history.

(56) References Cited

U.S. PATENT DOCUMENTS 8,262,560 B2    9/2012  Whitman
2002/0061131 A1    5/2002  Sawhney et al.
(Continued)

OTHER PUBLICATIONS

Shin et al. "Occlusion removal method of partially occluded 3D object using sub-image block matching in computational integral imaging", Optical Society of America, vol. 16, No. 21 / Optics Express, 2008 (Year: 2008).*

(Continued)

*Primary Examiner* — Randolph I Chu
(74) *Attorney, Agent, or Firm* — Carter, DeLuca & Farrell LLP

(57) ABSTRACT

The present disclosure is directed to systems and methods for removing an occluding object from a surgical image. An image capture device is inserted into a patient and captures an initial image of a surgical site inside the patient during a surgical procedure. A controller receives the image and determines that the occluding object is present in the initial image. The controller executes a removal algorithm that includes controlling the image capture device to perform a plurality of movements, controlling the image capture device to capture a plurality of images, wherein each image among the plurality of images corresponds to a movement among the plurality of movements, and applying an image filter to combine the initial image and the plurality of images and generate a processed image where the occluding object is removed from the processed image.

18 Claims, 7 Drawing Sheets

(51) Int. Cl.
  *G06T 5/00* (2006.01)
  *G06T 5/50* (2006.01)
  *A61B 34/00* (2016.01)
  *A61B 34/37* (2016.01)

(52) U.S. Cl.
  CPC ............. *G06T 5/50* (2013.01); *A61B 34/37* (2016.02); *A61B 2090/3612* (2016.02); *G06T 2207/10068* (2013.01); *G06T 2207/20212* (2013.01)

(56) References Cited

U.S. PATENT DOCUMENTS

| | | |
|---|---|---|
| 2006/0079752 A1 | 4/2006 | Anderl et al. |
| 2009/0103793 A1* | 4/2009 | Borland ............... G06T 15/08 382/131 |
| 2010/0312100 A1 | 12/2010 | Zarkh et al. |
| 2011/0125030 A1 | 5/2011 | Bai et al. |
| 2011/0273582 A1 | 11/2011 | Gayko et al. |
| 2011/0305388 A1 | 12/2011 | Wedi et al. |
| 2014/0288413 A1* | 9/2014 | Hwang ............... A61B 90/361 600/424 |
| 2015/0046818 A1 | 2/2015 | Wade |
| 2015/0238073 A1 | 8/2015 | Charles et al. |

OTHER PUBLICATIONS

Veld et al. "Detection and Handling of Occlusion in an Object Detection System", Proceedings of SPIE—The International Society for Optical Engineering, 2015 (Year: 2015).*
Y. Zhang, J. Xiao, M. Shah, \Motion Layer Based Object Removal in Videos, IEEE Workshop on Application on Computer Vision, Jan. 5-6, Breck-enridge, Colorado, 2005. (Year: 2005).*
Extended European Search Report dated Oct. 2, 2019 corresponding to counterpart Patent Application EP 17760499.8.
Forbin et al.: "Temporal Extension to Exemplar-based Inpainting Applied to Scratch Correction in Damaged Image Sequences", Visualization, Imaging, and Image Processing: Fifth IASTED International Conference Proceedings, Sep. 7, 2005, pp. 1-5, XP-002579645, ISBN: 978-0-88986-528-0.
International Search Report and Written Opinion corresponding to counterpart Int'l Appln. No. PCT/US2017/019257 dated Jun. 1, 2017.
Shinde et al.: "Pixelate Removal in an Image Fiber Probe Endoscope Incorporating Comb Structure Removal Methods"; J. Med. Imaging Health Inf. 4; pp. 202-211; Apr. 2014.
Criminisi, et al.: "Region Filling and Object Removal by Exemplar-Based Image Inpainting"; IEEE Transactions on Image Processing, vol. 13, No. 9; 13 pp; Sep. 2004.

* cited by examiner

SYSTEMS AND METHODS FOR REMOVING OCCLUDING OBJECTS IN SURGICAL IMAGES AND/OR VIDEO

CROSS-REFERENCE TO RELATED APPLICATIONS

This application is a U.S. National Stage Application filed under 35 U.S.C. § 371(a) of International Patent Application Serial No. PCT/US2017/019257, filed Feb. 24, 2017, which claims the benefit of and priority to U.S. Provisional Patent Application Ser. No. 62/302,366, filed Mar. 2, 2016, the entire disclosure of which is incorporated by reference herein.

BACKGROUND

Minimally invasive surgeries involve the use of multiple small incisions to perform a surgical procedure instead of one larger opening or incision. The small incisions have reduced patient discomfort and improved recovery times. The small incisions have also limited the visibility of internal organs, tissue, and other matter.

Endoscopes have been used and inserted in one or more of the incisions to make it easier for clinicians to see internal organs, tissue, and other matter inside the body during surgery. These endoscopes have included a camera with an optical and/or digital zoom capability that is coupled to a display showing the magnified view of organs, tissue, and matter inside the body as captured by the camera. When performing a minimally invasive surgical procedure, one or more surgical tools may be used with the endoscope. The endoscope's viewpoint has to be placed relative to the tool such that the tool does not impede the view of the surgical site. In the case of three dimension (3D) endoscopy, when the tools are too close to the lens and/or the tools are moving, a user may experience disorientation and/or nausea thereby forcing the user to constrain their movement choices. Additionally, local contaminants may obscure the lens thereby compromising portions of any image obtained by the endoscope.

There is a need for improved methods of providing a clinician with an endoscopic view that is not obscured by tool and/or local contaminants.

SUMMARY

The present disclosure is directed to systems and methods for removing an occluding object from a surgical image.

In an embodiment of the disclosure, a system for removing an occluding object from a surgical image includes an image capture device configured to be inserted into a patient and capture an initial image of a surgical site inside the patient during a surgical procedure and a controller configured to receive the image. When the controller determines that the occluding object is present in the initial image, the controller executes a removal algorithm. The removal algorithm includes controlling the image capture device to capture a plurality of images and applying an image filter to combine the initial image and the plurality of images and generate a processed image where the occluding object is removed from the processed image.

In some aspects, the removal algorithm further includes controlling the image capture device to perform a plurality of movements, wherein each image among the plurality of movements corresponds to a movement among the plurality of movements.

In some aspects, each movement among the plurality of movements includes a magnitude and a direction. Further, each movement among the plurality of movements is predetermined.

In an aspect, applying the image filter includes separating the initial image into an initial background image and an initial occluding layer, separating the plurality of images into a plurality of background images and a plurality of occluding layers, and combining the initial background images and the plurality of background images to generate the processed image. Combining the initial background images and the plurality of background images includes registering the initial background image and the plurality of background images, and overlaying the registered initial background image and the plurality of background images.

In other aspects, applying the image filter includes removing the occluding object from the initial image to create an empty space, registering the plurality of images with the initial image, and filling the empty space in the initial image with corresponding pixels from the registered plurality of images, wherein the corresponding pixels do not include the occluding object.

In some aspects, the controller determines that the occluding object is present in the initial image based on an input from a user.

In some aspects, a display displays the processed image.

In another embodiment of the present disclosure, a method for removing an occluding object from a surgical image is provided. The method includes capturing an initial image of a surgical site inside the patient during a surgical procedure with an image capture device and executing a removal algorithm when the occluding object is detected in the initial image. The removal algorithm includes controlling the image capture device to capture a plurality of images and applying an image filter to combine the initial image and the plurality of images and generate a processed image where the occluding object is removed from the processed image.

In some aspects, the removal algorithm further includes controlling the image capture device to perform a plurality of movements, wherein each image among the plurality of movements corresponds to a movement among the plurality of movements.

In some aspects, each movement among the plurality of movements includes a magnitude and a direction. Further, each movement among the plurality of movements is predetermined.

In an aspect, applying the image filter includes separating the initial image into an initial background image and an initial occluding layer, separating the plurality of images into a plurality of background images and a plurality of occluding layers, and combining the initial background images and the plurality of background images to generate the processed image. Combining the initial background images and the plurality of background images includes registering the initial background image and the plurality of background images, and overlaying the registered initial background image and the plurality of background images.

In other aspects, applying the image filter includes removing the occluding object from the initial image to create an empty space, registering the plurality of images with the initial image, and filling the empty space in the initial image with corresponding pixels from the registered plurality of images, wherein the corresponding pixels do not include the occluding object.

In some aspects, the processed image is displayed.

In yet another embodiment of the present disclosure, a system for removing an occluding object from a surgical image includes an image capture device configured to be inserted into a patient and capture an initial image of a surgical site inside the patient during a surgical procedure and a controller configured to receive the image. When the controller determines that the occluding object is present in the initial image, the controller executes a removal algorithm. The removal algorithm includes controlling the image capture device to capture a video feed including a plurality of images, generating a collection of substitution pixels based on the plurality of images included in the video feed, a location of the occluding object, and a point of view of the image capture device when the video feed is captured, and applying an image filter to combine the initial image and the plurality of images and generate a processed image where the occluding object is removed from the processed image based on the collection of substitution pixels.

BRIEF DESCRIPTION OF THE DRAWINGS

The above and other aspects, features, and advantages of the present disclosure will become more apparent in light of the following detailed description when taken in conjunction with the accompanying drawings in which.

DETAILED DESCRIPTION

Image data captured from an endoscope during a surgical procedure may be analyzed to remove occluding objects from the viewpoint of the endoscope. Various images of the surgical site may be obtained by moving the endoscope according to a predetermined plan. The various images may then be combined to present a single image or video to a user where the occluding object is removed from the image or video.

One or more of these technologies may be included as part of an imaging system in a surgical robotic system to provide a clinician with additional information within an endoscope's field of view. This may enable the clinician to quickly identify, avoid, and/or correct undesirable situations and conditions during surgery.

The present disclosure is directed to systems and methods for providing processed images in real time to a clinician during a surgical procedure where occluding objects are removed from the images. The systems and methods described herein apply image processing filters to a captured image to provide an image free of obscurities. In some embodiments, the systems and methods permit video capture during a surgical procedure. The captured video is processed in real time or near real time and then displayed to the clinician as processed image. The image processing filters are applied to each frame of the captured video. Providing the processed image or video to the clinician provides the clinician with an unobscured view to a clinician.

The embodiments described herein enable a clinician to view a region of interest with sufficient detail to ensure the effectiveness of a surgical procedure.

Figure 1:
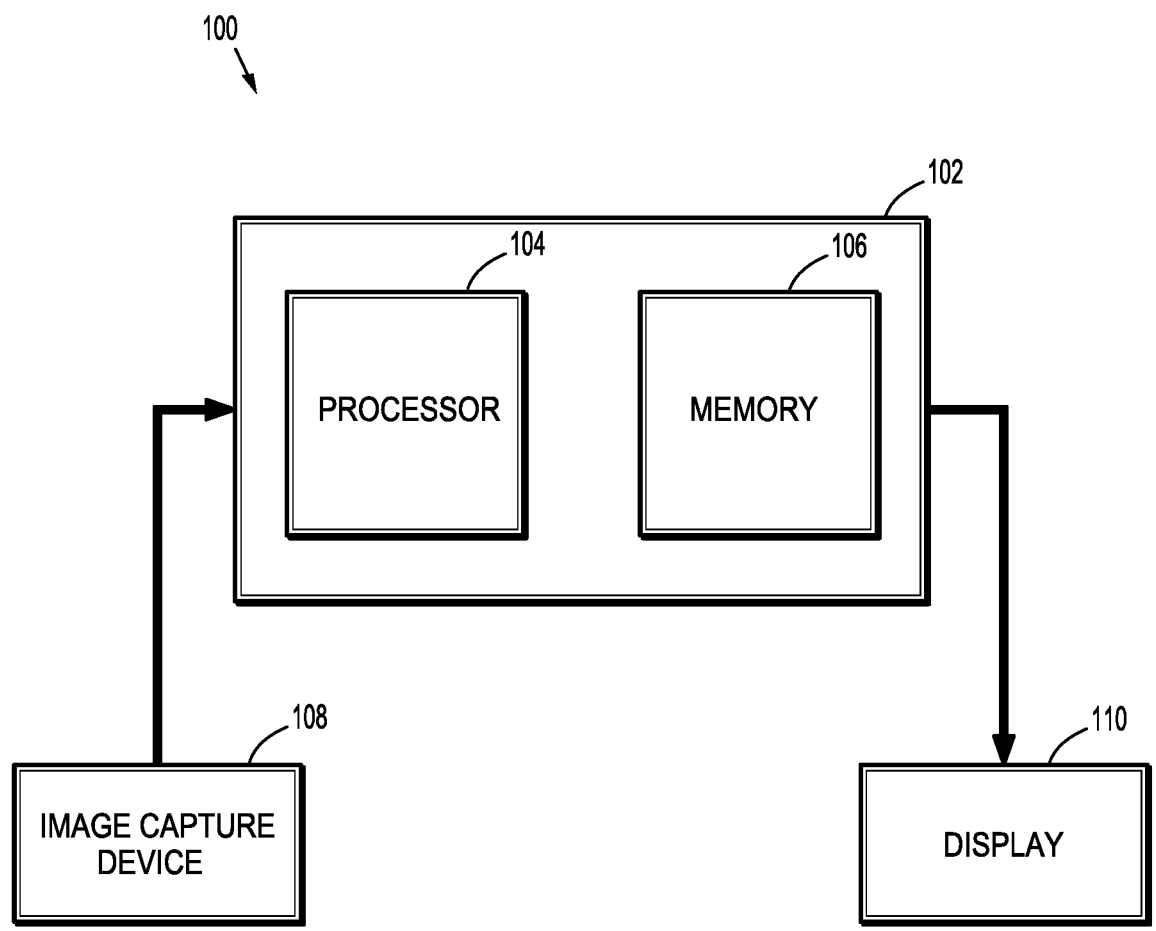
FIG. 1 is a block diagram of a system for removing occluding objects in a surgical environment in accordance with an embodiment of the present disclosure.

Turning to FIG. 1, a system for processing images and/or video of a surgical environment, according to embodiments of the present disclosure, is shown generally as 100. System 100 includes a controller 102 that has a processor 104 and a memory 106. The system 100 also includes an image capture device 108, e.g., a camera, that records still frame images or moving images. Image capture device 108 may be incorporated into an endoscope, stereo endoscope, or any other surgical toll that is used in minimally invasive surgery. A display 110, displays processed images to a clinician during a surgical procedure. Display 110 may be a monitor, a projector, or a pair of glasses worn by the clinician. In some embodiments, the controller 102 may communicate with a central server (not shown) via a wireless or wired connection. The central server may store images of a patient or multiple patients that may be obtained using x-ray, a computed tomography scan, or magnetic resonance imaging.

Figure 2:
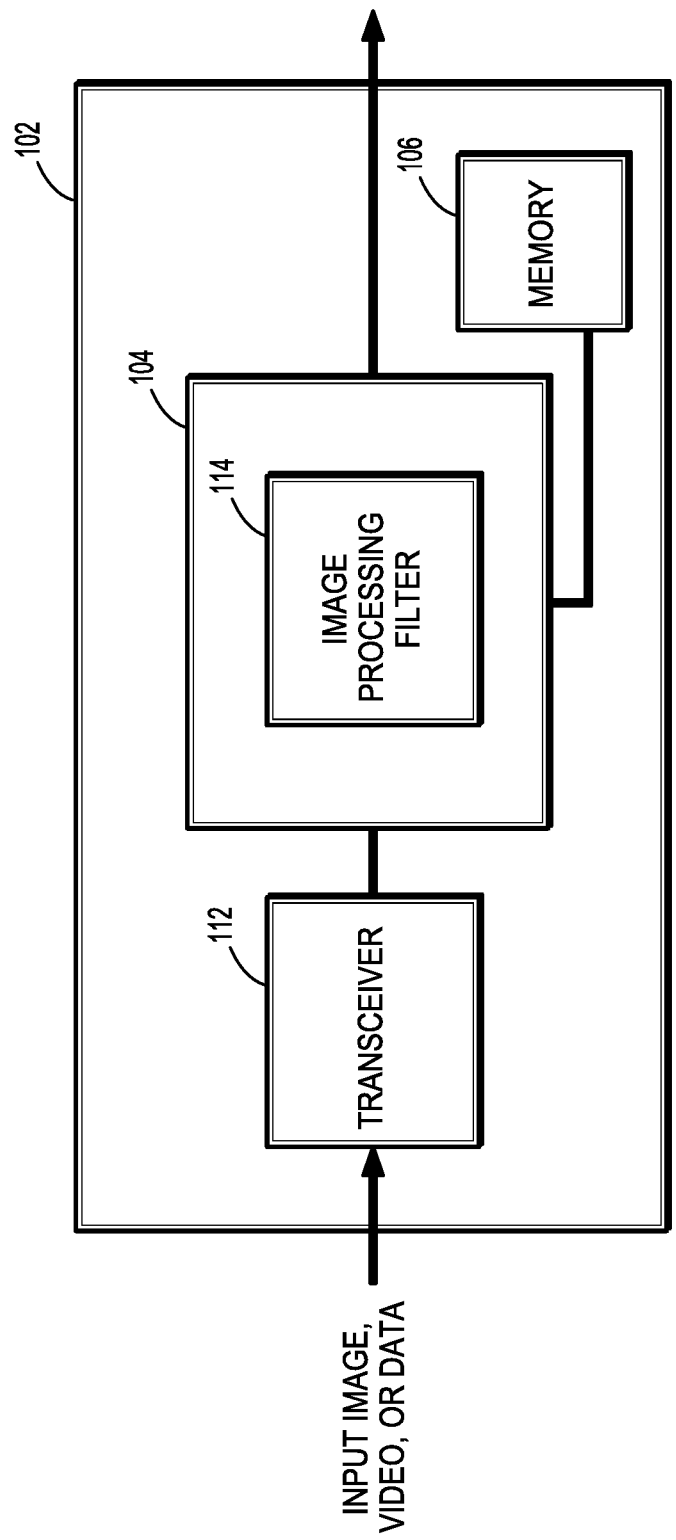
FIG. 2 is a block diagram of the controller of FIG. 1.

FIG. 2 depicts a system block diagram of the controller 102. As shown in FIG. 2, the controller 102 includes a transceiver 112 configured to receive still frame images or video from the image capture device 108. In some embodiments, the transceiver 112 may include an antenna to receive the still frame images, video, or data via a wireless communication protocol. The still frame images, video, or data are provided to the processor 104. The processor 104 includes an image processing filter 114 that processes the received still frame images, video, or data to generate a processed image or video. The image processing filter 114 may be implemented using discrete components, software, or a combination thereof. The processed image or video is provided to the display 110.

Figure 3A:
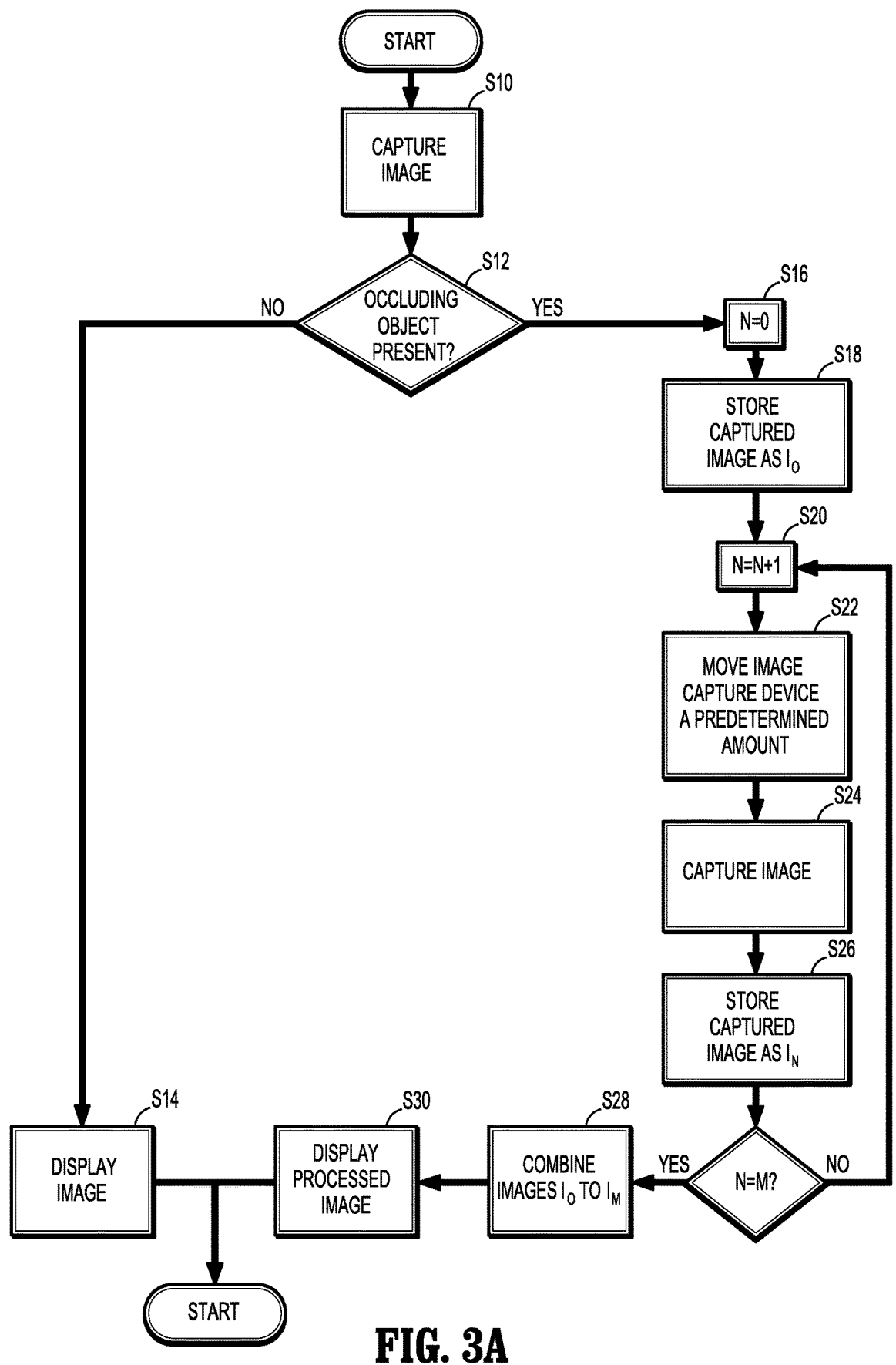
FIG. 3A is a flow chart depicting an image processing method for removing occluding objects in an image or video in accordance with an embodiment of the present disclosure.
Figure 4:
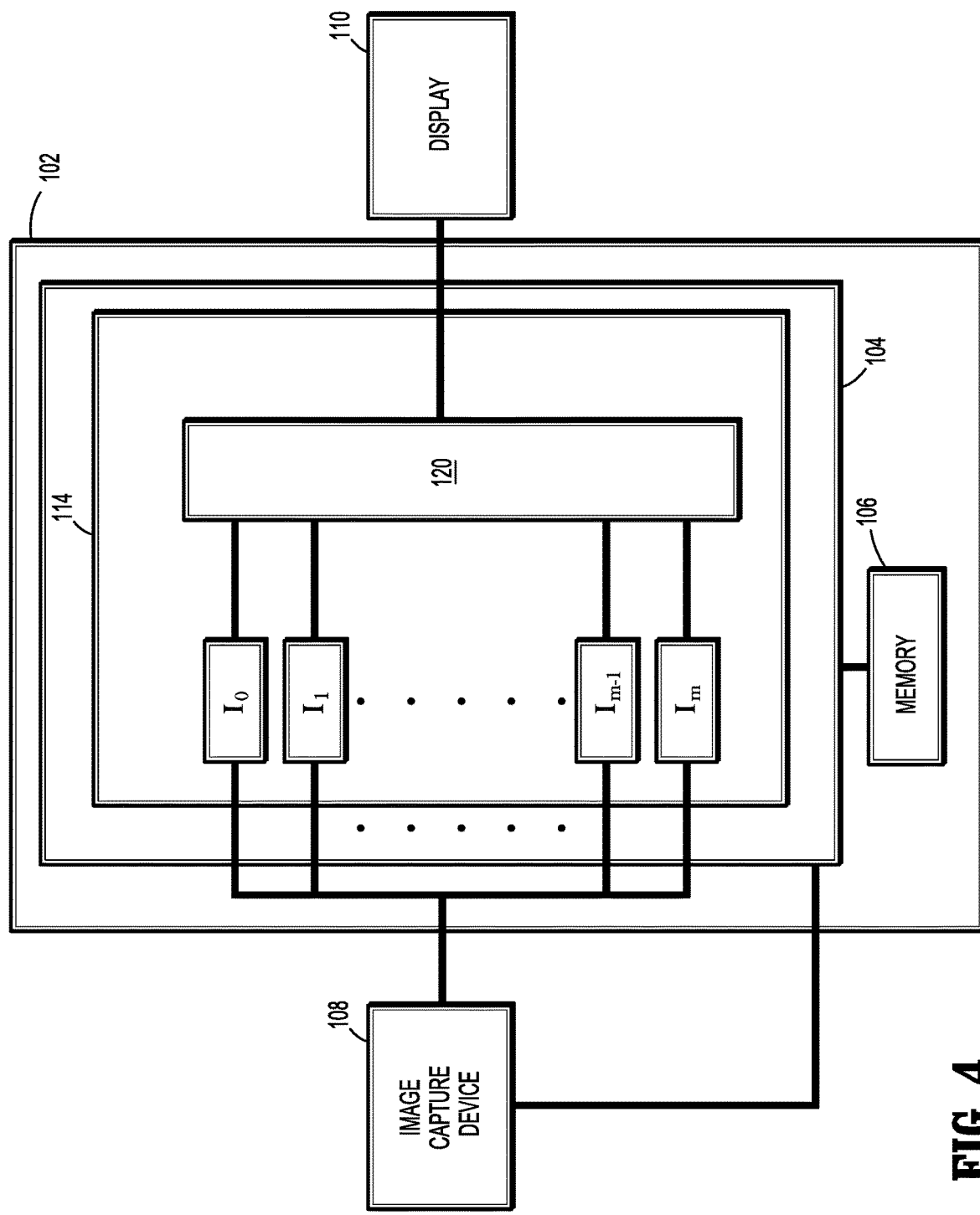
FIG. 4 is a block diagram of a system for removing occluding objects in an image or video in accordance with an embodiment of the present disclosure.

A system and method for removing occluding object will be described in more detail while making reference to FIGS. 3A and 4. As shown in FIGS. 3A and 4, the image capture device 108 captures an initial image in step s10. In step s12, the processor 104 determines if an occluding object is present. If an occluding object is not present, the process proceeds to step s14 where the image is displayed on display 110. If the processor 104 determines an occluding object is present, the processor 104 executes a removal algorithm stored in memory 10. The presence of the occluding object may be determined by the processor 104 using conventional image processing techniques or it may be determined by a user using a touch screen device or any other conventional methods for selecting an object on a display (e.g., a mouse, joystick, voice command, touch pad, etc.).

In step s16, a counter "N" is set to "0" and the image captured in step s10 set as "$I_0$" and transmitted to image processing filter 114. The counter "N" is incremented by one in step s20 and the processor then controls the image capture device 108 in step s22 to perform a plurality of movements of a predetermined magnitude and direction in order to obtain a plurality of images of the surgical site from different perspectives. Movement of the image capture device 108 may include moving the whole device or a lens (not shown)

in the device 108. Once the image capture device 108 is moved the predetermined amount, the image capture device 108 captures a new image in step s24 and stores the new image as "$I_N$". Steps s20 to s26 are repeated until the image capture device 108 captures and stores image "$I_M$", where "M" is a predetermined number of moves performed by the image capture device 108.

In step s28, the "M+1" images captured by the image capture device 108 are combined in image filter 120. The image filter 120 converts image "$I_0$" into a background image "$I_{B0}$", which includes an image of the surgical site, and an occlusion layer "$I_{L0}$", which includes the occluding object, using conventional image processing techniques. The image filter repeats the conversion for images "$I_1$" through "$I_M$" to generate background images "$I_{B1}$" through "$I_{BM}$" and occlusion layers "$I_{L1}$" though "$I_{LM}$". Images "$I_{B0}$" through "$I_{BM}$" would then be registered and overlaid on top of each other to produce a processed image to be displayed to a user in display 110 where the occluding object has been removed.

In another embodiment, in step s28, the occluding object may be removed from image "$I_0$" leaving an empty space in the image "$I_0$". The image filter 120 uses corresponding pixels from images "$I_1$" to "$I_M$" taken at different perspectives to fill in the empty space created in image "$I_0$" thereby producing a complete image of the surgical site without the occluding object. Specifically, image "$I_0$" and image "$I_1$" are compared by filter 120 to register or align the two images. Then image filter 120 uses the pixels in image "$I_1$" that do not belong to the occluding object to fill in the empty space in image "$I_0$". The process is repeated for the remaining images "$I_2$" to "$I_M$" until the empty space in image "$I_0$" is filled.

Figure 3B:
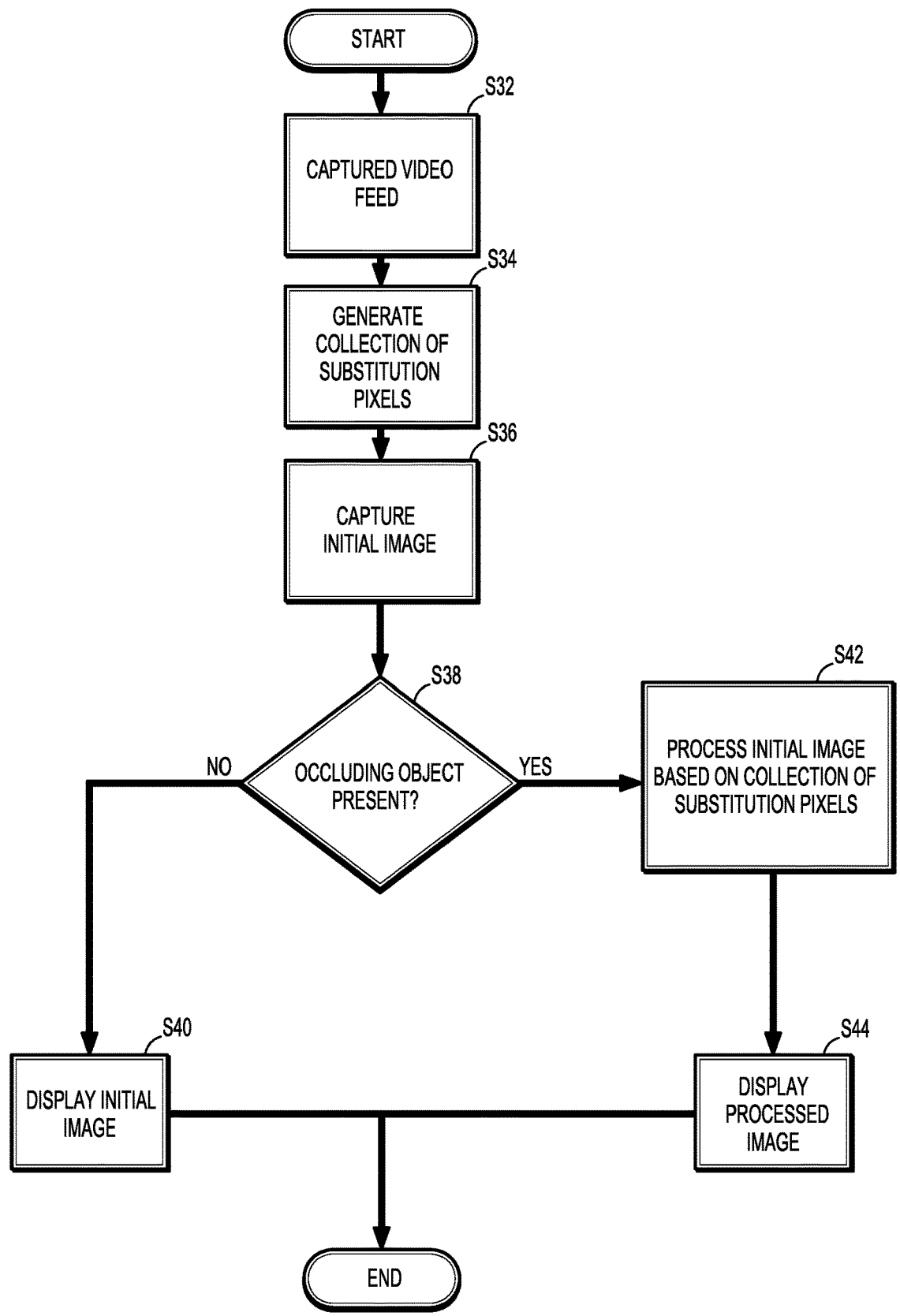
FIG. 3B is a flow chart depicting an image processing method for removing occluding objects in an image or video in accordance with another embodiment of the present disclosure.

In another embodiment, a plurality of images may be obtained over time to remove occluding objects. As shown in FIGS. 3B and 4, image capture device 108 captures a video feed over time where the video feed comprises a plurality of images in step s32. Processor 104 may then generate a collection of substitution pixels based on the plurality of images included in the video feed, the location of the occluding object(s), and the point of view of the endoscope when the video feed is captured in steps s34. The collection of substitution pixels may be stored in memory 106. In step s36, the image capture device 108 captures an initial image. In step s38, the processor 104 determines if an occluding object is present. If an occluding object is not present, the process proceeds to step s40 where the image is displayed on display 110. If the processor 104 determines an occluding object is present, the processor 104 executes a removal algorithm stored in memory 10 in step s42. In step s42, the image filter 120 processes the initial image using the collection of substitution pixels to remove the occluding object from the initial image to generate a processed image. In order to remove the occluding object from the initial image, the image filter 120 identifies pixels that belong to specific objects at specific spatial locations relative to the image capture device 108. The image filter 120 then removes the relatively nearer pixel(s) belonging to the occluding object, which is a pixel that is relatively closer to the image capture device 108, and substitutes the relatively nearer pixel(s) with relatively further pixel(s) from the collection of substitution pixels. The image is then reassembled with the relatively further pixel(s) in place of the relatively nearer pixel(s) to create the processed image. The processed image is then displayed on display 110 in step s44.

Figure 5:
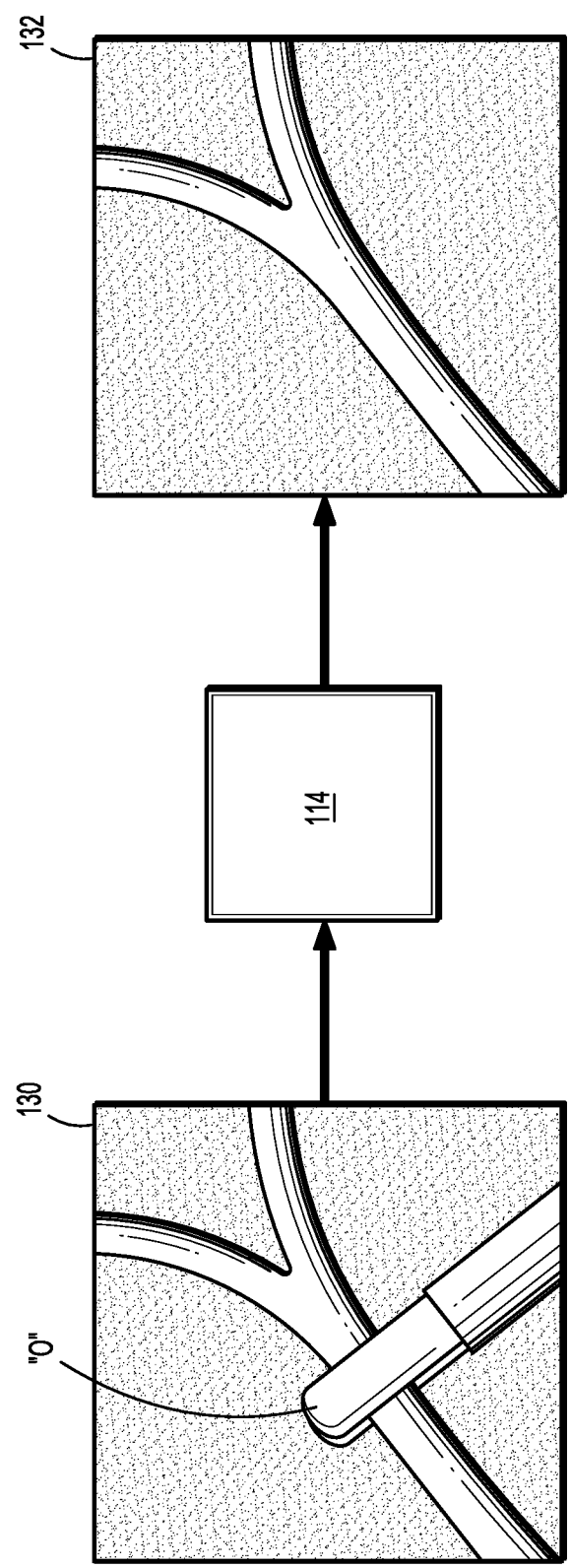
FIG. 5 shows an example of a captured image and a processed image.

FIG. 5 depicts an image 130 of a surgical environment that is captured by the image capture device 108. Image 130 is processed by image processing filter 114, which may involve the use of image filter 120, to generate a processed image 132. As can be seen in processed image 132, the occluded object "O" that was present in image 130 is removed from the processed image 132.

The above-described embodiments may also be configured to work with robotic surgical systems and what is commonly referred to as "Telesurgery." Such systems employ various robotic elements to assist the clinician in the operating theater and allow remote operation (or partial remote operation) of surgical instrumentation. Various robotic arms, gears, cams, pulleys, electric and mechanical motors, etc. may be employed for this purpose and may be designed with a robotic surgical system to assist the clinician during the course of an operation or treatment. Such robotic systems may include, remotely steerable systems, automatically flexible surgical systems, remotely flexible surgical systems, remotely articulating surgical systems, wireless surgical systems, modular or selectively configurable remotely operated surgical systems, etc.

Figure 6:
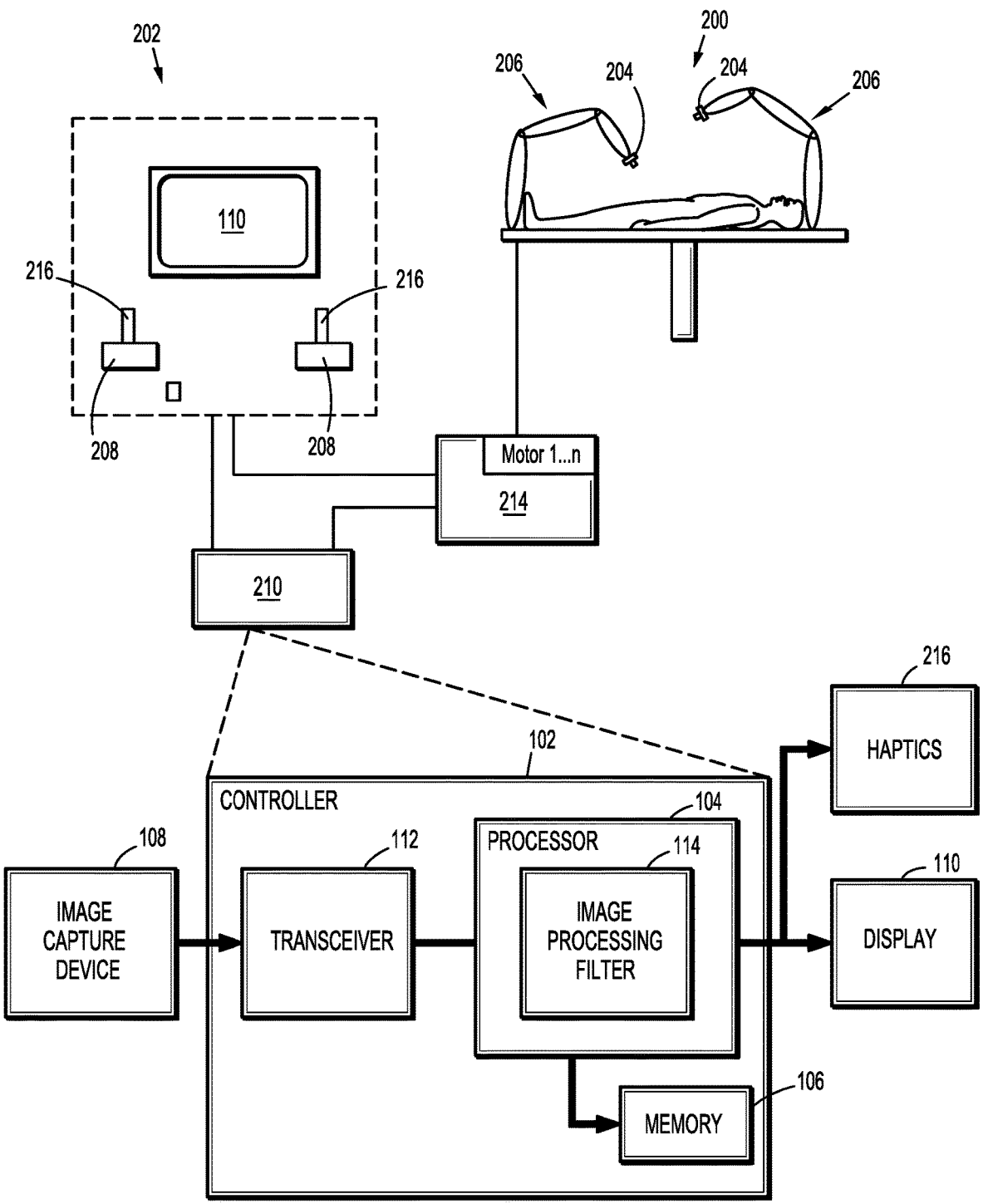
FIG. 6 is a system block diagram of a robotic surgical system in accordance with an embodiment of the present disclosure.

As shown in FIG. 6, a robotic surgical system 200 may be employed with one or more consoles 202 that are next to the operating theater or located in a remote location. In this instance, one team of clinicians or nurses may prep the patient for surgery and configure the robotic surgical system 200 with one or more instruments 204 while another clinician (or group of clinicians) remotely controls the instruments via the robotic surgical system. As can be appreciated, a highly skilled clinician may perform multiple operations in multiple locations without leaving his/her remote console which can be both economically advantageous and a benefit to the patient or a series of patients.

The robotic arms 206 of the surgical system 200 are typically coupled to a pair of master handles 208 by a controller 210. Controller 210 may be integrated with the console 202 or provided as a standalone device within the operating theater. The handles 206 can be moved by the clinician to produce a corresponding movement of the working ends of any type of surgical instrument 204 (e.g., probe, end effectors, graspers, knifes, scissors, etc.) attached to the robotic arms 206. For example, surgical instrument 204 may be a probe that includes an image capture device. The probe is inserted into a patient in order to capture an image of a region of interest inside the patient during a surgical procedure. One or more of the image processing filters 114A or 114B are applied to the captured image by the controller 210 before the image is displayed to the clinician on a display 110.

The movement of the master handles 208 may be scaled so that the working ends have a corresponding movement that is different, smaller or larger, than the movement performed by the operating hands of the clinician. The scale factor or gearing ratio may be adjustable so that the operator can control the resolution of the working ends of the surgical instrument(s) 204.

During operation of the surgical system 200, the master handles 208 are operated by a clinician to produce a corresponding movement of the robotic arms 206 and/or surgical instruments 204. The master handles 208 provide a signal to the controller 210 which then provides a corresponding signal to one or more drive motors 214. The one or more drive motors 214 are coupled to the robotic arms 206 in order to move the robotic arms 206 and/or surgical instruments 204.

The master handles 208 may include various haptics 216 to provide feedback to the clinician relating to various tissue parameters or conditions, e.g., tissue resistance due to manipulation, cutting or otherwise treating, pressure by the instrument onto the tissue, tissue temperature, tissue impedance, etc. As can be appreciated, such haptics 216 provide the clinician with enhanced tactile feedback simulating actual operating conditions. The haptics 216 may include vibratory motors, electroactive polymers, piezoelectric devices, electrostatic devices, subsonic audio wave surface actuation devices, reverse-electrovibration, or any other device capable of providing a tactile feedback to a user. The master handles 208 may also include a variety of different actuators 218 for delicate tissue manipulation or treatment further enhancing the clinician's ability to mimic actual operating conditions.

The embodiments disclosed herein are examples of the disclosure and may be embodied in various forms. Specific structural and functional details disclosed herein are not to be interpreted as limiting, but as a basis for the claims and as a representative basis for teaching one skilled in the art to variously employ the present disclosure in virtually any appropriately detailed structure. Like reference numerals may refer to similar or identical elements throughout the description of the figures.

The phrases "in an embodiment," "in embodiments," "in some embodiments," or "in other embodiments," which may each refer to one or more of the same or different embodiments in accordance with the present disclosure. A phrase in the form "A or B" means "(A), (B), or (A and B)". A phrase in the form "at least one of A, B, or C" means "(A), (B), (C), (A and B), (A and C), (B and C), or (A, B and C)". A clinician may refer to a surgeon or any medical professional, such as a doctor, nurse, technician, medical assistant, or the like performing a medical procedure.

The systems described herein may also utilize one or more controllers to receive various information and transform the received information to generate an output. The controller may include any type of computing device, computational circuit, or any type of processor or processing circuit capable of executing a series of instructions that are stored in a memory. The controller may include multiple processors and/or multicore central processing units (CPUs) and may include any type of processor, such as a microprocessor, digital signal processor, microcontroller, or the like. The controller may also include a memory to store data and/or algorithms to perform a series of instructions.

Any of the herein described methods, programs, algorithms or codes may be converted to, or expressed in, a programming language or computer program. A "Programming Language" and "Computer Program" includes any language used to specify instructions to a computer, and includes (but is not limited to) these languages and their derivatives: Assembler, Basic, Batch files, BCPL, C, C+, C++, Delphi, Fortran, Java, JavaScript, Machine code, operating system command languages, Pascal, Perl, PL1, scripting languages, Visual Basic, metalanguages which themselves specify programs, and all first, second, third, fourth, and fifth generation computer languages. Also included are database and other data schemas, and any other metalanguages. No distinction is made between languages which are interpreted, compiled, or use both compiled and interpreted approaches. No distinction is also made between compiled and source versions of a program. Thus, reference to a program, where the programming language could exist in more than one state (such as source, compiled, object, or linked) is a reference to any and all such states. Reference to a program may encompass the actual instructions and/or the intent of those instructions.

Any of the herein described methods, programs, algorithms or codes may be contained on one or more machine-readable media or memory. The term "memory" may include a mechanism that provides (e.g., stores and/or transmits) information in a form readable by a machine such as a processor, computer, or a digital processing device. For example, a memory may include a read only memory (ROM), random access memory (RAM), magnetic disk storage media, optical storage media, flash memory devices, or any other volatile or non-volatile memory storage device. Code or instructions contained thereon can be represented by carrier wave signals, infrared signals, digital signals, and by other like signals.

It should be understood that the foregoing description is only illustrative of the present disclosure. Various alternatives and modifications can be devised by those skilled in the art without departing from the disclosure. For instance, any of the processed images described herein can be combined into a single processed image to be displayed to a clinician. Accordingly, the present disclosure is intended to embrace all such alternatives, modifications and variances. The embodiments described with reference to the attached drawing figs. are presented only to demonstrate certain examples of the disclosure. Other elements, steps, methods and techniques that are insubstantially different from those described above and/or in the appended claims are also intended to be within the scope of the disclosure.

What is claimed is:

1. A system for removing an occluding object from a surgical image, the system comprising:
    an image capture device configured to be inserted into a patient and capture an initial image of a surgical site inside the patient during a surgical procedure; and
    a controller configured to receive an initial image from the image capture device, wherein, when the controller determines that the occluding object is present in the initial image, the controller executes a removal algorithm, wherein the removal algorithm includes:
        controlling the image capture device to capture a plurality of images; and
        applying an image filter to combine the initial image and the plurality of images and generate a processed image where the occluding object is removed from the processed image.

2. The system of claim 1, wherein the removal algorithm further includes controlling the image capture device to perform a plurality of movements, wherein each image among the plurality of movements corresponds to a movement among the plurality of movements.

3. The system of claim 2, wherein each movement among the plurality of movements includes a magnitude and a direction.

4. The system of claim 2, wherein each movement among the plurality of movements is predetermined.

5. The system of claim 1, wherein applying the image filter includes:
    separating the initial image into an initial background image and an initial occluding layer;
    separating the plurality of images into a plurality of background images and a plurality of occluding layers; and
    combining the initial background images and the plurality of background images to generate the processed image.

6. The system of claim 5, wherein combining the initial background images and the plurality of background images includes:

registering the initial background image and the plurality of background images; and overlaying the registered initial background image and the plurality of background images.

7. The system of claim 1, wherein applying the image filter includes:

removing the occluding object from the initial image to create an empty space;

registering the plurality of images with the initial image; and filling the empty space in the initial image with corresponding pixels from the registered plurality of images, wherein the corresponding pixels do not include the occluding object.

8. The system of claim 1, wherein the controller determines that the occluding object is present in the initial image based on an input from a user.

9. The system of claim 1, further comprising a display that displays the processed image.

10. A method for removing an occluding object from a surgical image, the method comprising:

capturing an initial image of a surgical site inside the patient during a surgical procedure with an image capture device; and executing a removal algorithm when the occluding object is detected in the initial image, the removal algorithm including:

controlling the image capture device to capture a plurality of images; and applying an image filter to combine the initial image and the plurality of images and generate a processed image where the occluding object is removed from the processed image.

11. The method of claim 10, wherein the removal algorithm further includes controlling the image capture device to perform a plurality of movements, wherein each image among the plurality of movements corresponds to a movement among the plurality of movements.

12. The method of claim 11, wherein each movement among the plurality of movements includes a magnitude and a direction.

13. The method of claim 11, wherein each movement among the plurality of movements is predetermined.

14. The method of claim 10, wherein applying the image filter includes:

separating the initial image into an initial background image and an initial occluding layer;

separating the plurality of images into a plurality of background images and a plurality of occluding layers; and combining the initial background images and the plurality of background images to generate the processed image.

15. The method of claim 14, wherein combining the initial background images and the plurality of background images includes:

registering the initial background image and the plurality of background images; and overlaying the registered initial background image and the plurality of background images.

16. The method of claim 10, wherein applying the image filter includes:

removing the occluding object from the initial image to create an empty space;

registering the plurality of images with the initial image; and filling the empty space in the initial image with corresponding pixels from the registered plurality of images, wherein the corresponding pixels do not include the occluding object.

17. The method of claim 10, further comprising displaying the processed image.

18. A system for removing an occluding object from a surgical image, the system comprising:

an image capture device configured to be inserted into a patient and capture a video feed including a plurality of images of a surgical site inside the patient during a surgical procedure; and a controller configured to generate a collection of substitution pixels based on the plurality of images included in the video feed, a location of the occluding object, and a point of view of the image capture device when the video feed is captured, wherein the image capture device captures an initial image of a surgical site inside the patient during a surgical procedure, and when the controller determines that the occluding object is present in the initial image, the controller executes a removal algorithm, wherein the removal algorithm includes applying an image filter to the initial image to generate a processed image where the occluding object is removed from the processed image based on the collection of substitution pixels.

* * * * *